US00PP11548P

United States Patent [19]

Amorao et al.

[11] Patent Number: Plant 11,548

[45] Date of Patent: Oct. 3, 2000

[54] STRAWBERRY PLANT NAMED 'BAEZA'

[75] Inventors: Amado Q. Amorao, Camarillo; Bruce D. Mowrey, La Selva Beach, both of Calif.; Kristie L. Gilford, Dover, Fla.; Joseph I. Espejo, Jr., Watsonville; Thomas M. Sjulin, Aromas, both of Calif.

[73] Assignee: Driscoll Strawberry Associates, Inc., Watsonville, Calif.

[21] Appl. No.: 08/858,426

[22] Filed: May 19, 1997

[51] Int. Cl.[7] ..... A01H 5/00

[52] U.S. Cl. ..... Plt./209

[58] Field of Search ..... Plt./209, 208

[56] References Cited

U.S. PATENT DOCUMENTS

P.P. 10,221 2/1998 Sjulin et al. ..... Plt./209

P.P. 10,534 8/1998 Sjulin et al. ..... Plt./209

P.P. 10,642 10/1998 Amorao et al. ..... Plt./209

*Primary Examiner*—Howard J. Locker

*Assistant Examiner*—Kent L. Bell

*Attorney, Agent, or Firm*—Pennie & Edmonds LLP

[57] ABSTRACT

This invention relates to a new and distinct variety of strawberry plant named 'Baeza', botanically identified as *Fragaria×ananassa* Duch. The closest known variety is 'Key Largo'. The new variety is fully everbearing. The new variety is distinguished from 'Key Largo' by its flat plant habit, medium to strong interveinal leaf-blistering, as long as broad length-to-width ratio of the terminal leaflet, rounded basal shape of the terminal leaflet, rounded teeth on the terminal leaflets, medium to dense petiole pubescence, outward pose of petiole hairs, medium flower size, medium length of the fruiting trusses, light red fruit flesh color and very early to early season of initial harvest.

3 Drawing Sheets

BACKGROUND OF THE INVENTION

The new variety of strawberry plant was selected as a seedling in a controlled breeding plot at a ranch in Monterey County, Calif., U.S.A., on or about May 1991. The new variety originated as a result of a controlled cross between the Driscoll Strawberry Associates, Inc. varieties named 'M1' and 'Z2' (both unpatented varieties of Driscoll Strawberry Associates, Inc.) in an on-going breeding program. The original seedling of the new variety was grown and asexually propagated by stolons at the nursery of Driscoll Strawberry Associates, Inc., in Shasta County, Calif. The new variety was further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Baeza' (formerly known as 'DX-3'). The variety is botanically identified at *Fragaria×ananassa* Duch. Among the characteristics which distinguish the new variety from other varieties of which we are aware are a combination of traits which include plant habit, interveinal leaf-blistering, the length-to-width ratio of the terminal leaflet, the basal shape of the terminal leaflet, the shape of the teeth on the terminal leaflet, petiole pubescence, pose of petiole hairs, flower size, length of the fruiting trusses, fruit flesh color, season of initial harvest and type of fruit bearing.

COMPARISON TO CLOSEST VARIETIES

The variety which we believe to be closest to 'Baeza' from those known to us is 'Key Largo' (U.S. Plant Pat. No. 8,649). There are several characteristics of the new variety that are different from, or not possessed by 'Key Largo'. For example, the plant habit of 'Baeza' is flat, while that of 'Key Largo' is flat globose. The interveinal blistering of the leaves of 'Baeza' is medium to strong, while that of 'Key Largo' is weak to medium. The length-to-width ratio of the terminal leaflet is as long as broad for 'Baeza', while that of 'Key Largo' is broader than long. The basal shape of the terminal leaflet of 'Baeza' is rounded, while it is obtuse on 'Key Largo'. The teeth on the terminal leaflet of 'Baeza' are rounded, while those of 'Key Largo' are obtuse. The petiole pubescence of 'Baeza' is medium to dense, while that of 'Key Largo' is sparse. The pose of the petiole hairs of 'Baeza' is outward, while that of 'Key Largo' is upward. The flower size of 'Baeza' is medium, while the flower size of 'Key Largo' is large. The fruiting truss of 'Baeza' is medium in length, while that of 'Key Largo' is long. The fruit flesh color of 'Baeza' is light red, while that of 'Key Largo' is medium red. The season of initial harvest for 'Baeza' is very early to early, while that of 'Key Largo' is early to mid-season. Lastly, 'Baeza' is fully everbearing, while 'Key Largo' is partially everbearing.

Regarding isozyme analysis, the phosphoglucoisomerase (PGI) isozyme banding pattern for 'Baeza' and 'Key Largo' is A1. The leucine aminopeptidase (LAP) isozyme banding pattern for 'Baeza' and 'Key Largo' is B3. The phosphoglucomutase (PGM) isozyme banding pattern for 'Baeza' is C3, while that for 'Key Largo' is C4. All isozyme analyses were conducted using leaf tissue. See *J. Amer. Soc. Hort. Sci.* 106:684 (1981).

TABLE 1

Isozyme Analysis for 'Baeza' and 'Key Largo'

| | Cultivar | |
|---|---|---|
| Locus | 'Baeza' | 'Key Largo' |
| PGI | A1 | A1 |
| LAP | B3 | B3 |
| PGM | C3 | C4 |

The 'Key Largo' isozyme data is from U.S. Plant Pat. No. 8,649.

BRIEF DESCRIPTION OF THE ILLUSTRATIONS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
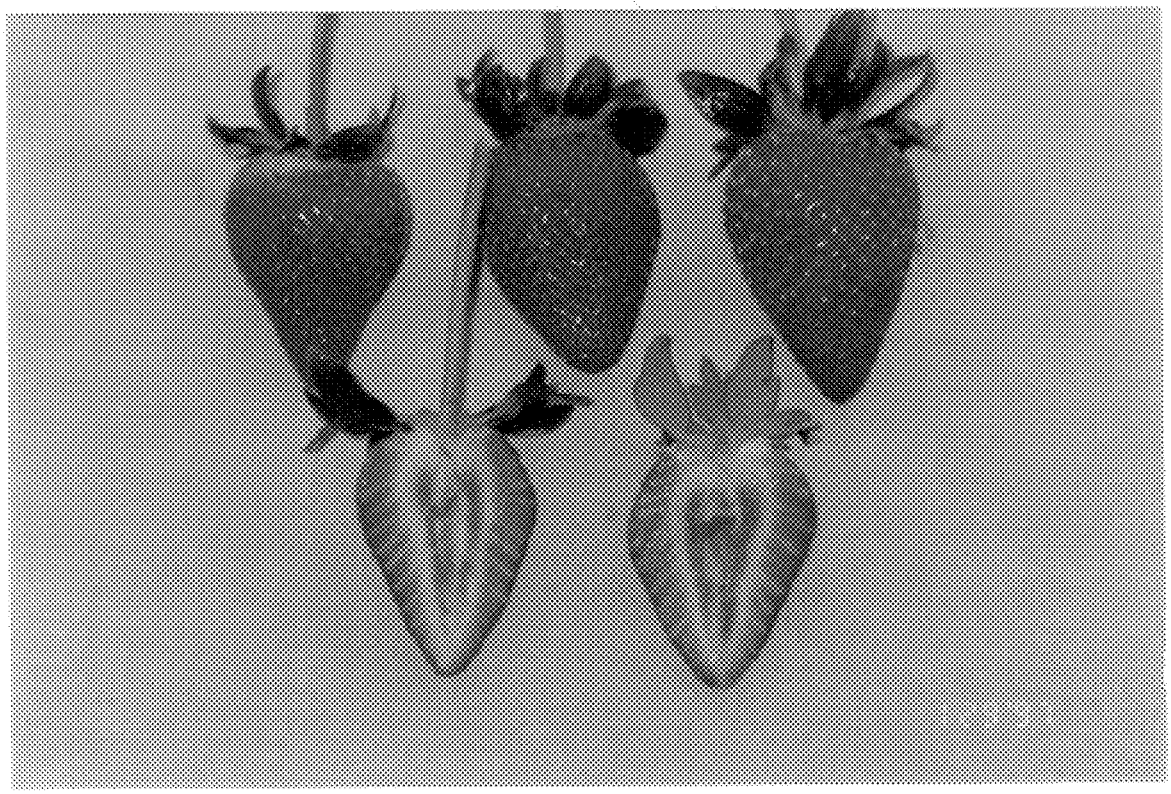
FIG. 1 shows typical whole fruit and the fruit in longitudinal section, illustrating the typical flesh and flesh coloration, core and shape of the new variety.
Figure 2:
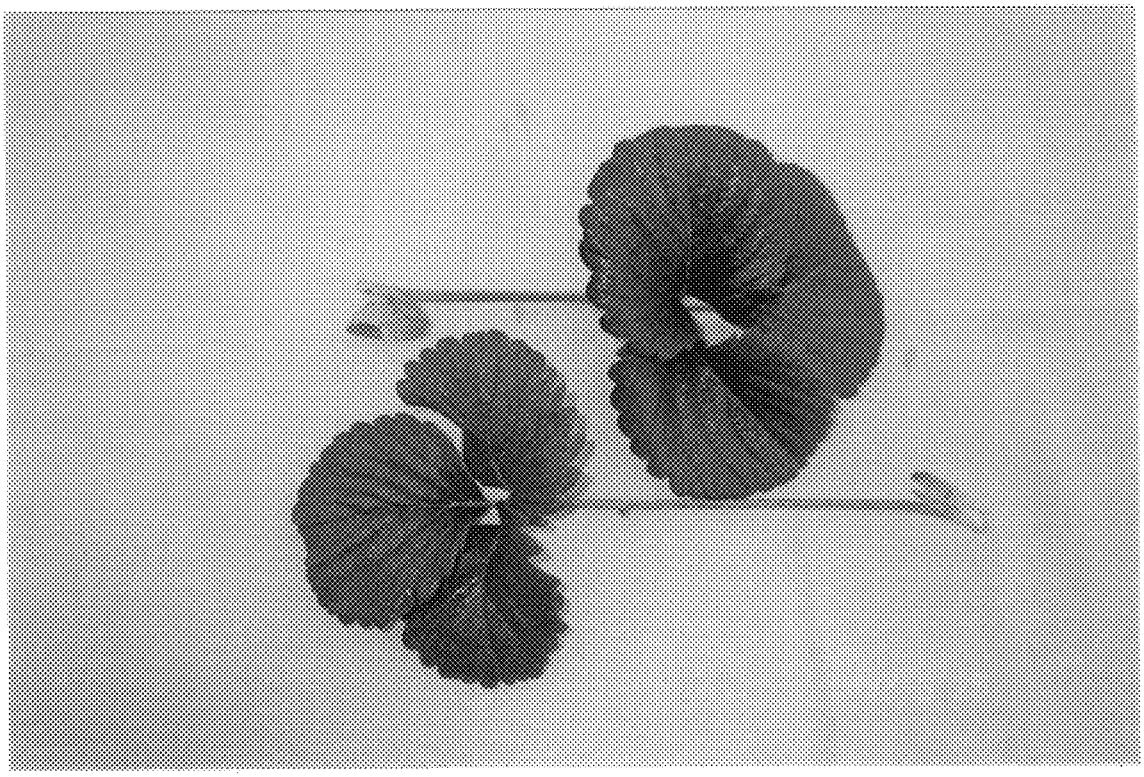
FIG. 2 shows the upper surface of two typical folioles of the new variety.
Figure 3:
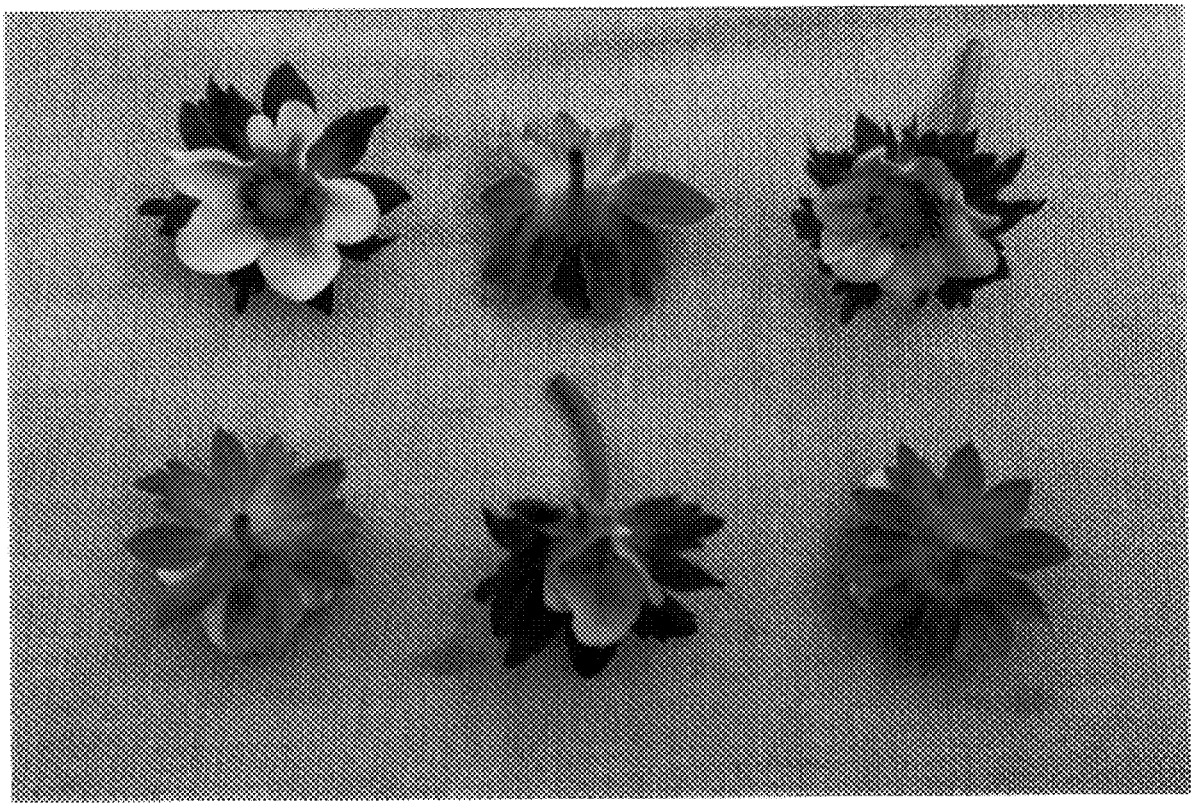
FIG. 3 shows the flowers and reproductive organs of the new variety, as well as the size and position of the petals and sepals.

The following detailed description of the new variety is based upon observations taken of plants and fruit grown in experimental test plots in 1997 at Garrison Farm in Hillsborough County, Fla., U.S.A. The strawberry varieties 'Baeza' and 'Key Largo' were planted on Oct. 9, 1996 and grown in similar conditions in a forcing system during the winter and were evaluated in a side-by-side comparison in January 1997. The measurements for grams/plant and fruit weight were taken at the Dolan Ranch, Ventura County, Calif. in the Fall of 1998; and additional measurements were taken at the Eiskamp Ranch, Monterey County, Calif. on Jul. 30, 1999. This description is in accordance with UPOV terminology. Color designations, color descriptions, and other phenotypical descriptions may deviate from the stated values and descriptions depending upon variation in environmental, seasonal, climatic and cultural conditions. Colors are described using standard Munsell Notation.

Propagation

The new variety is principally propagated by way of stolons. Although propagation by stolons is presently preferred, other known methods of propagating strawberry plants may be employed.

Characteristics of the New Variety

The following information is provided to describe the new variety.

Plant: The plants are medium in density with a flat habit and medium vigor. Specifically, at fruiting the average height and average width of 'Baeza' plants are 29.1 cm and 43.6 cm, respectively.

Leaves: The upperside of the leaves are medium to dark green with a Munsell color rating of 8.2GY 3.2/6.1. The underside of the leaves are gray-green which is not included on the Munsell Color Cascade.

The leaf profile is strongly concave to slightly concave with medium to strong interveinal blistering. The plants have three leaflets only. The terminal leaflet margin profile is revolute and the length-to-width ratio is as long as broad. The shape of the base of the terminal leaflet is rounded and the shape of the teeth on the terminal leaflet are rounded. The shape of the terminal leaflet is ovate to rounded. The terminal leaflet apex shape is rounded. The average terminal leaflet width is 8.8 cm. The average terminal leaflet length is 8.9 cm. The venation of the leaves is pinnate. The leaves have weak glossiness.

The petiole has medium to dense pubescence and the pose of the hairs is outwards. The average petiole length is 18.4 cm. The average petiole diameter is 0.5 cm. The Munsell color rating for petiole color is 5.3GY 5.2/9.7. The bracts occur on 58% of petioles, and the bracts typically occur in pairs. The average stipule length is 4.1 cm. The average stipule width is 1.4 cm.

Stolons: 'Baeza' has few to a medium number of thick stolons with strong anthocyanin coloration and medium pubescence.

Inflorescence: The positioning of the inflorescence is from beneath to level with the foliage. The flowers are of medium size. The average diameter of the primary and secondary flowers is 3.4 cm. The anther color is yellow with a Munsell color rating of 5.4Y 8.2/14.2. The average petal length is 1.2 cm. The average petal width is 1.3 cm. The petal color is white which is not included on the Munsell Color Cascade.

The average calyx diameter is 3.4 cm. On secondary flowers with 5 to 6 petals, the petals are overlapping. The petal length-to-width ratio on secondary flowers is as long as broad.

The fruiting trusses are medium in length and the attitude at first picking is semi-erect to prostrate. The average number of berries per fruiting truss is 8.5. The average yield is 379 g/plant as measured in the 1998 fruiting season which is an average yield for a strawberry variety grown in this season. The fruiting trusses branch at the middle of the inflorescence. The frequency of branching is moderate to high.

Fruit: Observations of the fruit were taken of secondary fruits on one year old plants. Strawberry plants possess a branching inflorescence, or peduncle, having a primary (first) flower which is the largest and secondary flowers which are on the lateral branches. "Secondary fruit" are those that develop from secondary flowers which develop from lateral buds on the peduncle. One year old plants are those which are in their first year in the fruiting field. The fruits are predominantly conical in shape. The fruit have a ratio of length to maximum width which ranges from longer than broad to much longer than broad. The fruit are large in size. The average length and diameter of the primary and secondary fruit are 3.8 cm and 3.4 cm, respectively. The average weight of the fruit is 21.2 g/berry as measured in the 1998 fruiting season. There is a slight difference in fruit shape between the primary and secondary fruits. The band without achenes is narrow. The fruit surface has a weak unevenness.

Fruit color: 'Baeza' skin color is red with a Munsell color rating of 6.8R 2.6/9.4 and has medium to strong glossiness. The fruit skin color is slightly uneven to even.

The insertion of the achenes is from level with the surface to above the surface of the fruit.

The calyx is inserted level with the fruit and the pose of the calyx segments is reflexed. The adherence of the calyx to the fruit is strong.

The fruit flesh is firm when fully ripe. The color of the fruit flesh is light red with a Munsell color rating of 7.1R 5.3/16.7. The flesh color is uneven to slightly uneven.

The fruit has a strong sweetness, with medium acidity and fine texture. The achenes are yellow (Munsell color rating 8.5YR 7.8/11.8) but darken to a red color when exposed to sunlight (Munsell color rating of 5.5R 2.9/11.6).

The time of flowering when 50% of the plants are at first flower is very early to early. When the 'Baeza' variety was planted in Florida in early October, the plants began flowering in late October to early November.

The harvest maturity when 50% of the plants possess ripe fruit is very early to early. For 'Baeza' planted in Florida in early October, 50% of the plants possessed ripe fruit in late November.

'Baeza' is a fully everbearing variety producing fruit. Everbearing strawberry varieties are characterized as plants which fruit two or more times per season, and the summer flowering is governed by long photoperiods. See *Advances in Fruit Breeding,* page 86 (eds. Jules Janick and James N. Moore, 1975).

Chilling requirements: 'Baeza' requires 4 to 6 weeks of chilling when planted in a winter plant cultural system.

Resistance to Stress

The new variety 'Baeza' is moderately resistant to drought, high temperatures, high pH and high soil salt levels.

Disease Resistance and Susceptibility

The 'Baeza' fruit is moderately resistant to decay by Botrytis fruit rot. 'Baeza' is moderately susceptible to leaf spots (*Xanthamonus fragariae*). The 'Baeza' plant is also moderately resistant to powdery mildew.

The 'Baeza' variety is susceptible to injury by the two-spotted spider mite (*Tetranychus urticae*), *Tarsonemus pallidus, Aphelencoides fragariae,* Aphis spp., and lygus bug (*Lygus hesparus*).

What is claimed is:

1. A new and distinct variety of strawberry plant, substantially as shown and described.

* * * * *